US007220594B2

(12) United States Patent
Foster et al.

(10) Patent No.: US 7,220,594 B2
(45) Date of Patent: *May 22, 2007

(54) METHOD AND APPARATUS FOR SORTING PARTICLES WITH A MEMS DEVICE

(75) Inventors: John S. Foster, Santa Barbara, CA (US); John C. Harley, Santa Barbara, CA (US); Steven H. Hovey, Goleta, CA (US); Richard T. Martin, Goleta, CA (US); Hung D. Nguyen, Los Angeles, CA (US); Paul J. Rubel, Santa Barbara, CA (US)

(73) Assignee: Innovative Micro Technology, Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/196,291

(22) Filed: Aug. 4, 2005

(65) Prior Publication Data

US 2005/0282151 A1 Dec. 22, 2005

Related U.S. Application Data

(63) Continuation-in-part of application No. 10/978,947, filed on Nov. 1, 2004, which is a continuation-in-part of application No. 10/189,607, filed on Jul. 8, 2002, now Pat. No. 6,838,056.

(51) Int. Cl.
*G01N 1/10* (2006.01)
*G01N 21/64* (2006.01)

(52) U.S. Cl. .................. 436/180; 436/43; 436/46; 436/63; 436/149; 436/164; 436/165; 436/172; 422/82.01; 422/82.05; 422/82.08; 422/100; 435/29; 435/30; 435/287.1; 435/288.3; 435/288.4; 435/288.5; 435/288.7; 209/3.1; 209/552; 209/576

(58) Field of Classification Search .................. 436/43, 436/46, 63, 149, 150, 164, 165, 172, 177, 436/180; 422/68.1, 73, 82.01, 82.05, 82.08, 422/100, 101, 103; 435/20, 30, 287.1, 288.3–288.5, 435/288.7, 29; 209/3.1, 552, 576
See application file for complete search history.

(56) References Cited

U.S. PATENT DOCUMENTS 5,837,200 A 11/1998 Diessel et al.

(Continued)

FOREIGN PATENT DOCUMENTS

WO WO 01/19516 3/2001

(Continued)

OTHER PUBLICATIONS

Gawad et al. Lab on a Chip, vol. 1, 2001, pp. 76-82.

(Continued)

*Primary Examiner*—Maureen M. Wallenhorst
(74) *Attorney, Agent, or Firm*—Jaquelin K Spong

(57) ABSTRACT

A micromechanical particle sorting chip uses laser light directed through at least one of a reflective and refractive surface to come to a focus in an optically transparent layer. The laser light impinges on a particle of interest, causing it to fluoresce. Upon detecting the fluorescence, a micromechanical actuator is activated, which directs the particle of interest into one of a plurality of possible exit paths.

20 Claims, 11 Drawing Sheets

U.S. PATENT DOCUMENTS

| | | |
|---|---|---|
| 5,971,355 A | 10/1999 | Biegelsen et al. |
| 6,100,541 A * | 8/2000 | Nagle et al. ................. 250/573 |
| 6,303,885 B1 | 10/2001 | Hichwa et al. |
| 6,438,279 B1 * | 8/2002 | Craighead et al. ............ 385/12 |
| 6,593,749 B2 | 7/2003 | Foster et al. |
| 6,692,952 B1 | 2/2004 | Braff et al. |
| 6,802,489 B2 * | 10/2004 | Marr et al. ............ 251/129.14 |
| 6,808,075 B2 | 10/2004 | Bohm et al. |
| 6,808,683 B2 | 10/2004 | Gilbert |
| 6,838,056 B2 * | 1/2005 | Foster ........................ 422/100 |
| 6,849,459 B2 | 2/2005 | Gilbert et al. |
| 6,877,528 B2 | 4/2005 | Gilbert et al. |
| 6,878,271 B2 | 4/2005 | Gilbert et al. |
| 6,883,957 B2 | 4/2005 | Gilbert et al. |
| 2005/0036920 A1 | 2/2005 | Gilbert |
| 2005/0092658 A1 | 5/2005 | Bohm et al. |
| 2005/0092662 A1 | 5/2005 | Gilbert et al. |
| 2005/0128479 A1 | 6/2005 | Gilbert et al. |

OTHER PUBLICATIONS

Blankenstein et al. Biosensors and Bioelectronics, vol. 13, Nos. 3-4, 1998, pp. 427-438.

Fu et al. Analytical Chemistry, vol. 74, No. 11, Jun. 1, 2002, pp. 2451-2457.

Baechi et al. Sensors and Actuators A, vol. 95, Jan. 1, 2002, pp. 77-83.

* cited by examiner

METHOD AND APPARATUS FOR SORTING PARTICLES WITH A MEMS DEVICE

CROSS REFERENCE TO RELATED APPLICATIONS

This U.S. patent application is a continuation-in-part of U.S. patent application Ser. No. 10/978,947, filed Nov. 1, 2004 which is a continuation-in-part of U.S. patent application Ser. No. 10/189,607 filed Jul. 8, 2002, now U.S. Pat. No. 6,838,056. Each of these applications is incorporated herein by reference in its entirety for all purposes.

STATEMENT REGARDING FEDERALLY SPONSORED RESEARCH

Portions of the present invention were made with U.S. Government support under DARPA Grant No. DAMD17-02-2-0067. The government may have certain rights in this invention.

STATEMENT REGARDING MICROFICHE APPENDIX

Not applicable.

BACKGROUND

This invention relates to the sorting of particles, such as biological cells. More particularly, this invention relates to a microelectromechanical systems (MEMS) particle sorting chip used to sort a component of interest from the rest of the fluid sample.

Many new therapies for cancer patients relate to enabling them to better withstand the challenge made to their bodies by the chemotherapies. In particular, it has recently been found that the inability of some patients to cope with chemotherapies has to do with the destruction of hematopoietic stem cells (HSCs), as ancillary damage of the chemotherapy. HSCs are the progenitor cells found in bone marrow, peripheral blood and many lymphoid organs. HSCs are responsible for generating the immune system components, such as T-cells, as well as the vital components of blood. When HSCs are destroyed in sufficient numbers, it becomes difficult for patients to replace blood cells, resulting in anemia often suffered by patients. The destruction of HSC's is also a leading cause of death in radiation victims, as the progenitor cells are destroyed, thereby destroying the ability to regenerate the vital components of the blood and immune systems.

Recent research has indicated however that if the human hematopoietic stem cells are removed from the patients' bodies prior to their receiving chemotherapy, and then replaced after the chemotherapy, the human hematopoietic stem cells are shielded from the effects of the chemotherapy. By reinfusing the human hematopoietic stem cells after the chemotherapy is finished, the patients' ability to regenerate their blood cells is regained and their resilience to the therapy is greatly enhanced. As a result, higher dosages of the chemotherapy can be administered to patients with better chances of diminishing the viability of the cancer cells, and yet the patients are able to regraft their blood-forming HSCs, which have been protected from exposure to the chemotherapy.

Until recently, the standard treatment for patients requiring blood-forming system reconstitution after chemotherapy was a bone marrow transplant (BMT). Bone marrow transplants require up to 100 withdrawals of marrow from the hip bone by large needles and the subsequent reinfusion of large volumes of cells and other fluid. These procedures are highly invasive, cumbersome, expensive and pose additional risks to the patient.

Mobilized peripheral blood (MPB), which accomplishes the same post-chemotherapy reconstitution with less trauma to the donor, can be generated in most patients by injecting a granulocyte colony-stimulating factor (G-CSF) that causes the body to produce a sufficient quantity of hematopoietic stem cells (HSCs). These cells migrate from the bone marrow to the blood, from which they are harvested in a sufficient quantity in a single 2-4 hour session that only requires vein access.

Both the bone marrow extractions and mobilized peripheral blood from cancer patients contain the hematopoietic stem cells necessary for reconstitution; however, they also contain large numbers of cancer cells, which are reinfused into the patient along with the human hematopoietic stem cells after the chemotherapy treatment. Logic and an increasing body of literature suggest that this reintroduction of cancer cells is one cause of the limited survival improvement associated with high dose chemotherapy and cell transplant.

Therefore, technology was developed to obtain highly purified non-cancerous HSCs from mobilized peripheral blood; i.e., the purification process eliminates the cancer cells, but retains the healthy stem cells necessary for reconstitution. The purification process also reduces the transfusion volume to less than 0.1 ml, in contrast to the 500-1500 ml of cells in fluid volume for BMT and MPB. The purification process is performed by flow cytometry, which separates the constituents of a fluid sample mixture according to fluorescence detected from the constituents. Purity of the resulting HSC product was 95% by this method, with no detectable cancer cells, and further details of the methodology can be found in Negrin et al., "Transplantation of Highly Purified CD34$^+$Thy-1$^+$ Hematopoietic Stem Cells in Patients with Metastatic Breast Cancer", Biology of Blood and Marrow Transplantation 6:262-271 (2000). For patients undergoing this HSC reinfusion treatment, the 5-year survival rate for women with advanced metastatic breast cancer jumped from 5% to about 50%.

Another application for HSC sorting is protection against nuclear radiation effects. The procedure would be to sort HSCs from individuals who potentially could be exposed at some later date to nuclear radiation. The human hematopoietic stem cells are frozen and can survive in that state essentially forever. If the individual is exposed, as could be the case in a nuclear plant accident or warfare, the human hematopoietic stem cells are then shipped to the patient's location, rapidly thawed, and then re-inserted into the patient. This procedure has been shown to save animals exposed to otherwise lethal doses of radiation.

However for these treatments to become practical, it must be learned how to sort large quantities of viable hematopoietic stem cells from the other constituents of the blood, with high concentration and high purity. An estimate of the number of stem cells required is $4 \times 10^6$ stem cells/kg body weight. The present separation process, flow cytometry, uses a high-pressure nozzle to separate tiny droplets containing the cells. The cell suspension is brought to the nozzle assembly under positive pressure, and introduced to the center of the sheath flow. The properties of fluid laminar flow focus the cell suspension into a single file, which is confined to the center of the fluid jet. Droplets are formed as the fluid exits the nozzle, and the droplets pass through one or more laser beams, which irradiate the cells and excite fluorescent markers with which the cells are tagged. The droplets are then given an electric charge to separate the droplets containing HSCs from those containing other constituents of the blood, as detected by fluorescence of the tagged molecules. The droplets are separated by passing them between a pair of electrostatic plate capacitors, which deflect the charged droplets into a sorting receptacle. The time-of-flight of the droplet through these stages requires careful calibration so that the sorting efficiency and effectiveness can be optimized.

Among the difficulties with the process is speed, as throughputs are limited to about 40,000 events per second. The rate is limited by the amount of pressure that the cells can withstand without damaging their viability, and the flow rate is proportional to the pressure. The fluidic settings which control the conditions of operation of the flow cytometers are interrelated. The nozzle diameter, system pressure and droplet frequency are independently set, whereas the jet velocity is related to the system pressure and nozzle diameter. Therefore the droplet time-of-flight must be set by empirical calibration with a standard sample. Therefore, not only are the systems themselves quite expensive, they require trained engineering staff to operate effectively. And lastly, contamination of the vessels with old sample tissue is a problem, as the equipment is difficult to sterilize. Decontamination issues encourage the use of disposable vessels, for which these machines are presently not designed. The high pressures used in the machines favor permanent fixturing of the plumbing in the tools. Also the careful alignment required of the receptacles with the trajectories of the droplets favors the permanent installation of the receptacles. About 7000 such systems exist worldwide today, and tend to be research tools rather than production equipment which can be used for clinical sorting in treating patients.

SUMMARY

Therefore, a need exists for a separation technique that solves throughput, cost, and disposability issues associated with present methods. This disclosure describes a novel device and method based on microelectromechanical systems (MEMS). MEMS devices are micron-sized structures which are made using photolithographic techniques pioneered in the semiconductor processing industry. Due to their small size and the batch fabrication techniques used to make the structures, they are capable of massive parallelism required for high throughput. These same features make them relatively inexpensive to fabricate, so that a disposable system is a realistic target for design.

The MEMS particle sorting chip described herein has a fluid channel defined in an optically transparent substrate, and a plurality of MEMS actuators disposed beneath a channel formed between the fluid channel and a plurality of exit paths. A particle of interest is detected by irradiating a fluid stream in the fluid channel and detecting the resulting fluorescence emanating from the particle of interest. When a particle of interest is detected, the MEMS actuator is activated, which closes one exit path and opens another, thereby directing the particle of interest into a sort/save reservoir, rather than a waste/return reservoir.

The MEMS particle sorter described herein may include a set of focusing optics which focus the laser light to a point in the fluid channel near but before the MEMS actuators. The focusing optics may include a refractive optical element and a reflective optical element, integrally created in the MEMS cell sorter chip. Furthermore, the cell sorter chip may also include a small aperture, which limits the ability of an imaging camera to acquire laser-induced fluorescence until the cell or fluid component of interest is located within the aperture. This combination of focusing optics and optical aperture may locate the particle of interest in the fluid channel with high precision, allowing the MEMS actuator to be opened at precisely the correct time to correctly sort a target cell or component of interest.

The MEMS particle sorting chip may be applied to sorting a component of interest from the rest of a fluid sample, for example, separating human hematopoietic stem cells from a blood sample. The MEMS particle sorting chip may include at least one fluid channel defined in an optically transparent layer, at least one of a reflective surface and a refractive surface formed in the optically transparent layer, which focuses light to a focal point within the fluid channel, and at least one micromechanical actuator defined on a substrate, disposed to act at a point downstream of the focal point within the fluid channel, to direct a particle into one of a plurality of possible exit paths.

BRIEF DESCRIPTION OF THE DRAWINGS

The present invention will be understood more fully from the following detailed description, and from the accompanying drawings, which however, should not be taken to limit the invention to the specific embodiments shown but are for explanation and understanding only.

DETAILED DESCRIPTION

Figure 1:
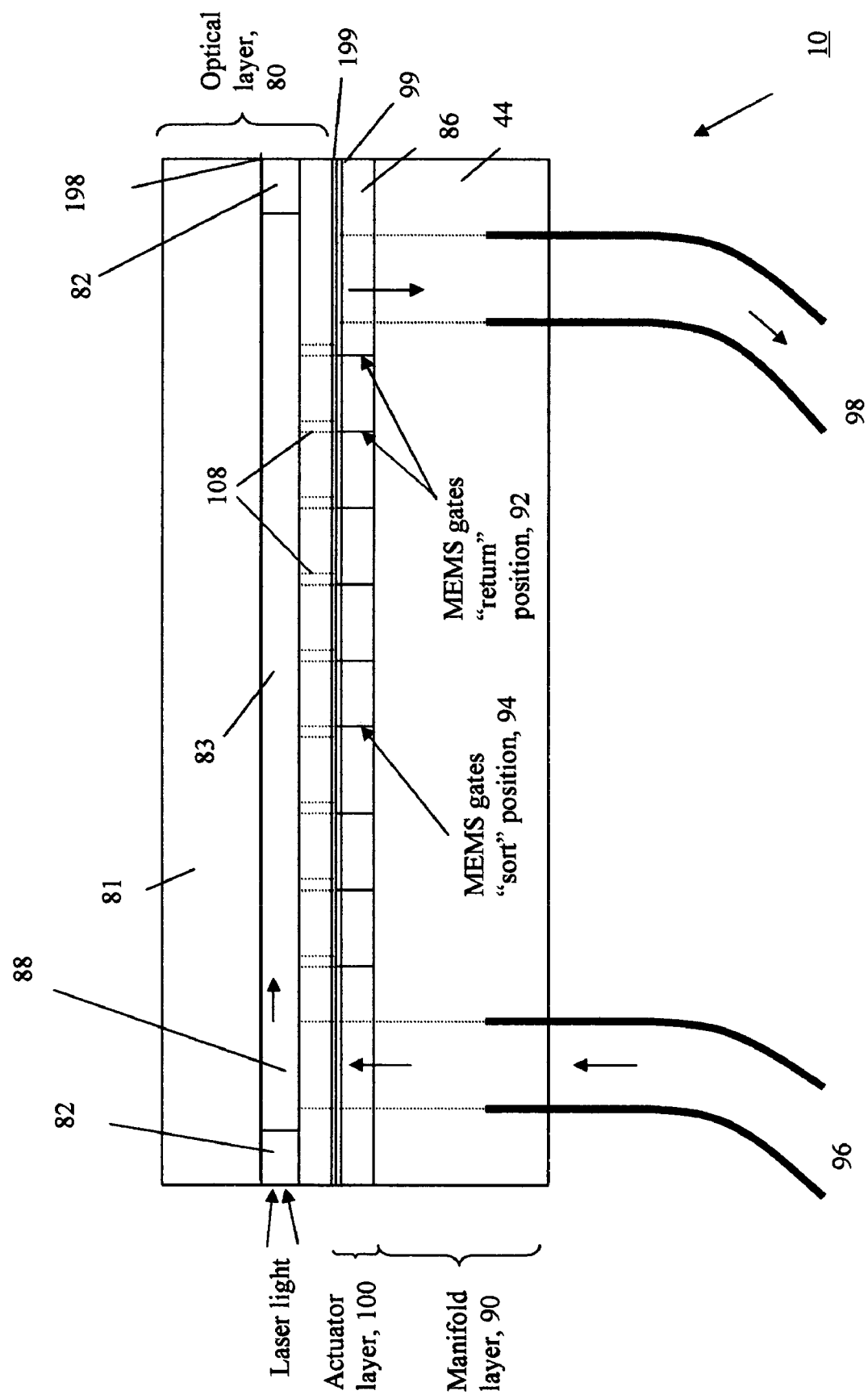
FIG. 1 is a simplified side view of the MEMS particle sorting chip, showing the light channel layer and reflective layers in detail.

The systems and methods set forth herein are described with respect to a particular embodiment, that of a cell sorter for sorting particular cells from a sample of human blood. However, it should be understood that the systems and methods may be applicable to a wide range of sorting applications, wherein it is desired to separate a particular component of interest from a remainder of a suspending fluid.

The MEMS device is an array of parallel inlet channels fabricated in a wafer, wherein the 25 um diameter of each channel is just large enough to admit the passage of a hematopoietic stem cell. (Hematopoietic stem cells are typically between 5 and 10 um in diameter.) At the exit from each parallel channel is an independent valve/actuator. The actuator directs the cells individually into one of two of different possible pathways, which are microfluidic channels etched into the wafer, beneath the parallel channels. The situation is shown schematically in FIG. 1. The figure shows the application of the device to the separation of the components of human blood, in this case the separation of hematopoietic stem cells (HSCs) from a fluid mixture of other cells. The actuator separates the sample stream into one of two manifolds, depending on the detection of a laser-induced fluorescence signal or multiple signals, depending on the fluorescent markers used. The presence of fluorescence or multiple fluorescence indicates that a human hematopoietic stem cell is detected, and the actuator directs the cell into a stem cell manifold with its stem cell receptacle. The receptacle may contain a cushion of fresh serum for sustaining viability of the cells collected.

The use of fluorescent markers to tag biological cells is known in the art. A wide variety of fluorescent markers exist which may be conjugated as labels to antibodies specific to cellular markers which identify particular sets and subsets of cells. Fluorescent markers which are available include fluorescein, Texas Red, phycobiliproteins, cyanine derivatives and rhodamine. For example, Negrin et al. ("Transplantation of Highly Purified CD34+Thy-1+Hematopoietic Stem Cells in Patients with Metastatic Breast Cancer", Biology of Blood and Marrow Transplantation 6:262-271 (2000)) reported that simultaneous detection of antigens CD34 and Thy-1 have good correlation to the presence of human hematopoietic stem cells. The lack of fluorescence indicates the cell is another constituent of the mixture, and not the tagged component. The occurrence of fluorescence indicates that the component of interest is present. In the case of detection of multiple fluorescent markers simultaneously, in some cases more than one laser may be used to excite the markers.

The sample cells may be dispersed in any convenient medium which can maintain viability such as phosphate-buffered saline, containing 0.1% to 0.5% fetal calf serum. The cells may have been subjected to pre-treatment, such as removal of cells by filtering, centrifugation, affinity separation or other technique which provides enrichment of the population of cells of interest. In addition, the cells may be diluted to avoid cells being concentrated too close to each other. The fluid mixture is then introduced to the MEMS device under positive pressure, through the inlet via 96, and out through the outlet via 98. The positive pressure is chosen to select the proper flow rate through the MEMS chip, and can be set and fixed for the duration of the use of the chip. The MEMS chip wafer 10 may include an optical cover 81 which is a barrier to the fluid mixture as well as an optically transparent element which allows the fluorescent signals to leave the chip and be detected outside the chip. A spacer layer 82 may separate optical cover 81 from the actuator layer 100, and define the thickness of the channel through which the fluid mixture flows before it enters one of the parallel channels, 108. Alternatively, optically transparent layer 88 may be an optically transparent solid layer, with fluid channels defined therein, in which case, the spacer layers 82 may not be needed. The parallel channels 108 may then be formed in a thin separate substrate, coupled to the optically transparent layer 88.

As the fluid mixture enters through the inlet via, it may flood the optically transparent layer 88 which lies between the optical cover 81 and the active layer substrate 44. Although optically transparent layer 88 is depicted in FIG. 1 as a simple void flooding the opening of each parallel channel 108 in parallel, it should be understood that optically transparent layer 88 may also include a plurality of well-defined fluid paths formed in the optical layer. In this case, the fluid path may route a portion of the flow from blood input 96 to each one of the parallel channels 108, for example. The optically transparent layer 88 may also include optical elements to further focus the light in the plane of the optically transparent layer 88, as will be described further below. Optically transparent layer 88 may be sandwiched between two reflecting layers, light reflecting layers 198 and 199. The function of the optically transparent layer 88 is to guide laser light in a quasi-two-dimensional sheet, exposing the cells in the fluid mixture only before the cells fall into the parallel channels 108. The fluid mixture flows from the optically transparent layer 88 into the parallel channels. The parallel channels may have been formed under the optically transparent layer 88 by lithographic patterning and etching, and provide a defined region 108 for delivering the fluid stream to the MEMS actuator layer 86. In optically transparent layer 88, the cells interact with the laser beam, and the cells of interest, which have been appropriately tagged with fluorescent markers, fluoresce as a result. The fluorescence is detected outside the MEMS chip and the fluorescing cell is mechanically separated from the other cells in the mixture, by the action of the MEMS actuator. The valve labeled 94 is in the sort/save position corresponding to the presence of a human hematopoietic stem cell, whereas the valves labeled 92 are in the waste/return position.

Figure 2:
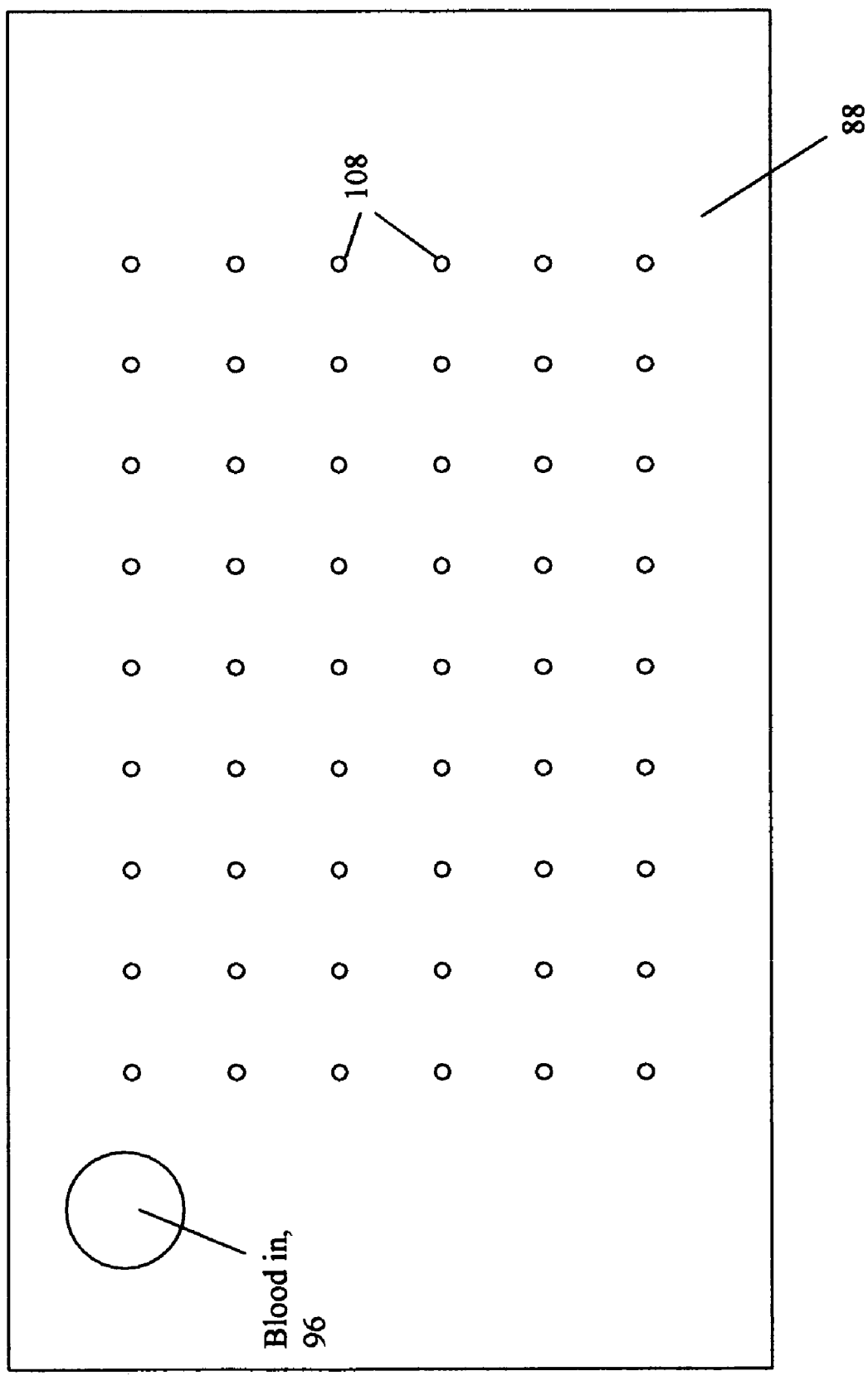
FIG. 2 is a plan view of the top surface of the MEMS particle sorting chip, showing the optically transparent light channel layer, as seen through the optical cover.

The top view of optically transparent layer 88 is shown in detail in FIG. 2, including the parallel channels, 108. The sample mixture is delivered to the top surface of FIG. 2 by the inlet via, 96, from which it filters down through the parallel channels 108 to the actuator/manifold layer. As with FIG. 1, optically transparent layer 88 is depicted as a simple void, although it should be understood that optically transparent layer 88 may also include well-defined channels feeding each of the parallel channels 108 with fluid from the fluid input 96. As shown in FIG. 2, the optical layer may include an n×m array of parallel channels, where n and m are, for example 32. Alternatively, as described further below, the optical layer, as well as the corresponding actuator and manifold layers, may be a one-dimensional array, for example, a 1×32 array of parallel channels 108. The manifold layer 90 and actuator layer 100 are shown in plan view in FIG. 3, and they lie just beneath the optical layer 80.

Figure 3:
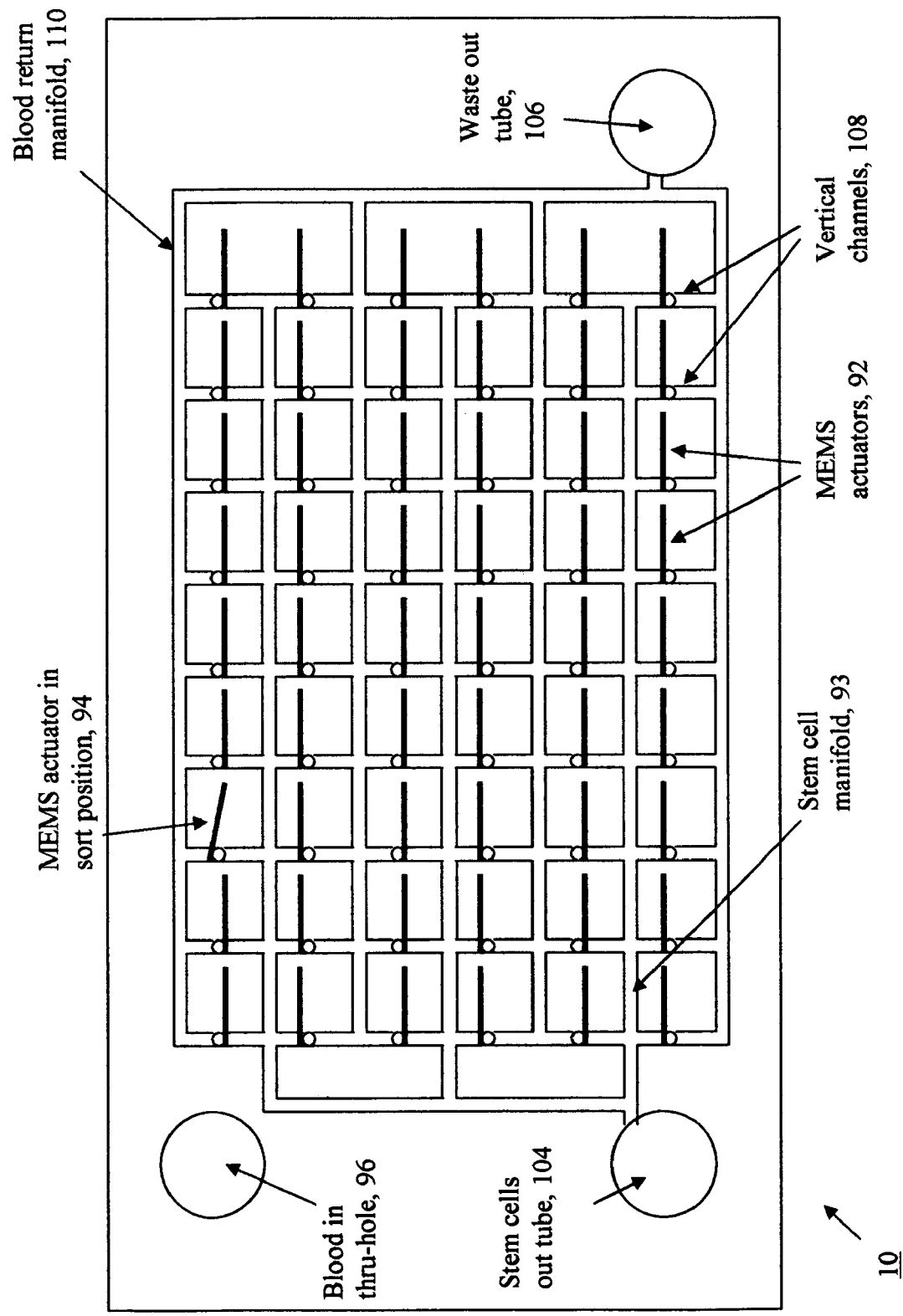
FIG. 3 is a plan view of the actuator/manifold layer of the MEMS particle sorting chip, showing the sorting manifolds.

The actuators are shown diagrammatically as the plurality of structures 92, lying at the exit of each parallel channel. As in FIG. 1, each of the actuators 92 shown is in the "waste" or "return" positions, directing the cells into the blood return manifold 110, with the exception of actuator 94, which is in the sort/save position. This actuator directs a fluorescing cell into the stem cell manifold 93, and the remaining actuators 92 direct non-fluorescing cells into the blood return manifold 110. After being properly herded into the stem cell manifold, the cell follows the fluid stream under positive pressure, until it reaches the stem cell out tube 104 leading to the stem cell receptacle, or the waste out tube 106 leading to the waste receptacle if it is a non-fluorescing cell. The dual manifolds have been patterned in the MEMS substrate, by lithographic means, as is shown in FIG. 3. The manifolds are sealed at the top by eutectic layer 99, which lies between bottom light reflecting layer 199 and the MEMS actuator layer 86.

The timing of fluorescence detection, actuation and actuation back to the nominal position 92 is important so as to allow only the fluorescing cell to be sorted and minimize the chance that an errant, non-fluorescing cell be sorted mistakenly. In the nominal case, the flow rate through each channel is roughly 0.2 meter per second. Before the cell enters the parallel channel 108, it is illuminated by the laser light and begins fluorescing. The fluorescing light is detected in the first 100-200 us, and the actuator is immediately (with small computer/controller delay of only tens of microseconds) moved into position shown as sort position 94. This actuation takes approximately 100 us. Therefore, the actuator is in the sort position just as the cell is approaching the MEMS actuator layer 86. MEMS actuator layer 86 is also approximately 30 um thick. After actuation from position 92 to 94, the actuator pauses in the sort position for only 100 us, and then returns to the default position 92. In one embodiment, the actuator can move back by the restoring force of a hingedly mounted spring. In another embodiment, it is actively actuated, back to the default position 92.

In order to maximize the flow of the fluid mixture without excessive pressures, the MEMS chip utilizes a large number of parallel channels flowing through the plane of the wafer as well as across the plane of the wafer. The large number of short path, parallel channels through the wafer has the advantage that very large pressure gradients are not needed to obtain reasonable flow rates. The device is designed so that the dominant pressure drop is generated in the parallel channel/actuator region 108 only, and care is taken to provide a uniform pressure head preceding the parallel channels and a minimum back pressure after the actuator region as the flow opens up into the larger manifolds. The device also does not need to create or manipulate a fine spray of droplets; instead the flow is continuous. With the actuator acting as a low inertia knife-edge gate valve, relatively low forces are needed to perform the sorting. This keeps the sample rate high with the reasonable voltages applied, on the order of 50 V. The tool is designed to be a low cost, special purpose machine sorting into two buckets only, but the concept is extendable to other applications.

Figure 4:
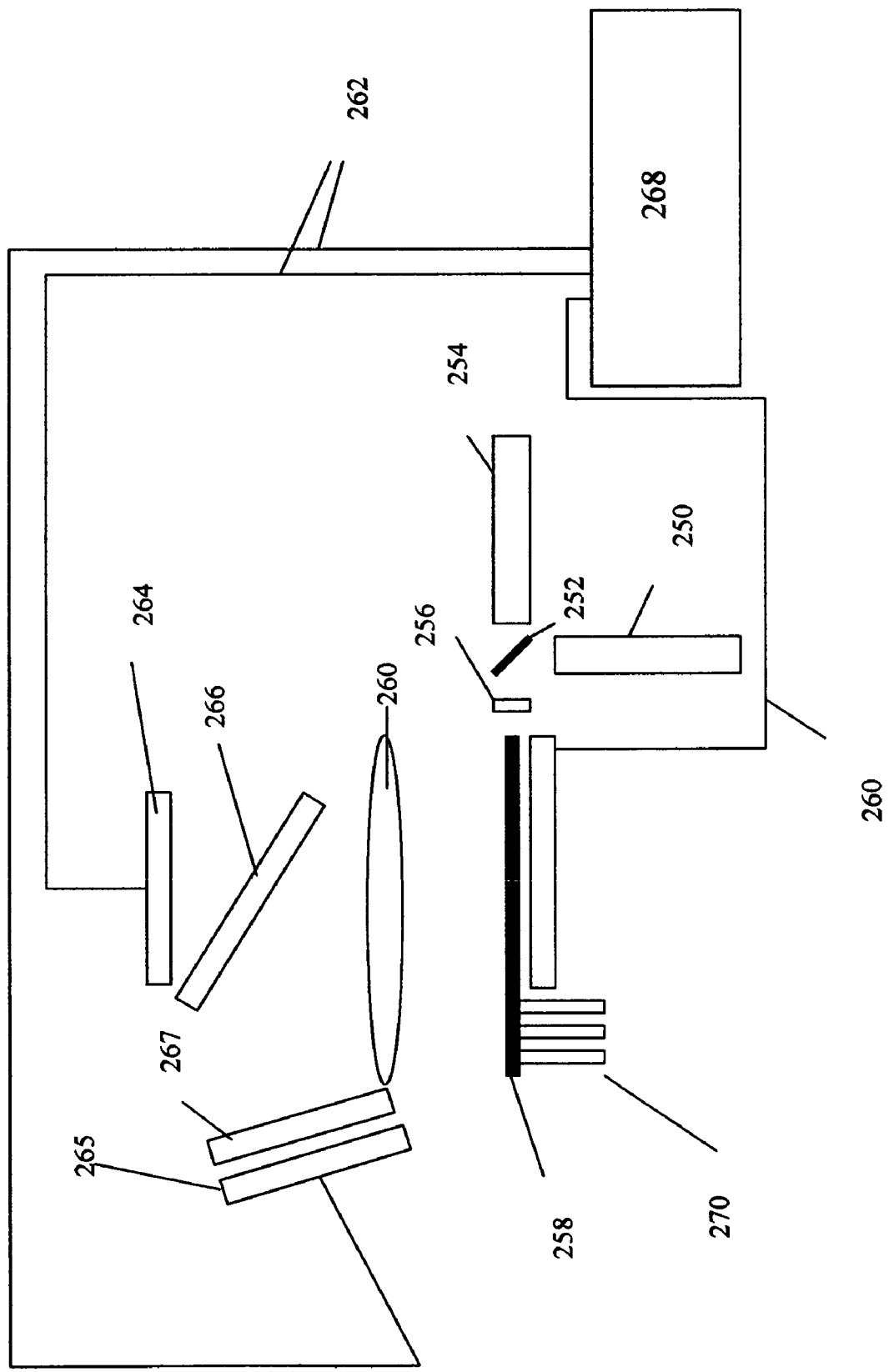
FIG. 4 is a simplified diagrammatic view of the MEMS particle sorting system.

The details of the optical system are shown in FIG. 4. Two lasers may be used to allow the flexibility to induce fluorescence in multiple markers: i.e. a first $Ar^+$ laser operating at 488 nm, and the second a Rhodamine 6-G dye laser operating at 590 nm. The beams may be combined with a beamsplitter/turning mirror 252, and focused into a line on the optically transparent layer 88 by a cylindrical lens 256. The two dimensional sheet of light propagates within the optically transparent layer 88. Fluorescent light emanating from above the parallel channels 108 (if an appropriate fluorescing cell is present) passes out of the MEMS chip through optical cover 81 and the collection lens 260 directs an image of the chip surface onto a set of light detectors 264 and 265, through the set of filters 266 and 267. The light detectors 264 and 265 may be charge coupled device (CCD) cameras or photomultiplier (PMT) tubes, for example. The filters are used to select only the desired fluorescence signal of the marker. In the case of sorting HSCs in which both CD34 and Thy-1 antigens are used, the filters are selected to pass only the wavelengths for the tags for those antigens, respectively. In general, then, the camera detectors are in the dark except during the rare events of detection of a fluorescence signal. The detection of fluorescence by the light detector (or the simultaneous detection of both signals, one in each camera) indicates the presence of a human hematopoietic stem cell in the sample manifold, at the position in the array indicated by the light detectors. The electronics then causes the appropriate actuator to be energized, diverting the sample cell into the appropriate manifold. The actuator is then positioned back to its initial state.

In the implementation described herein, the fluorescent light passing through collection lens 260 impinges first on one filter, filter 266. Light of the proper wavelength passes through filter 266 into the first high speed light detector 264. All other light reflects from the surface of filter 266, and impinges on filter 267. Light of the proper wavelength for that filter passes through into the second high speed light detector 265. In this way, efficient use is made of the available light to optimize signal-to-noise and speed in the system.

A variety of state-of-the-art camera systems are available to serve as the high-speed light detectors. For example, Photron USA (San Diego, Calif.) markets the PhotoCAM 250 CL, a monochrome camera with 10,000 frames per second performance (adequate for the 100 micro-second requirement in this invention) with over 4000 pixels in each frame, sufficient for this application. Although this high speed camera is not as sensitive as photo-multiplier tubes commonly used in modern cell-sorters, gain comes from the longer integration time in the current invention, ten times longer than the cell sorters, so that adequate signal-to-noise is achieved using cameras. If additional sensitivity is required for a particular application, an intensifier plate can be added in front of the camera's detector. These are common in industry, known as microchannel plates (MCP), and are an array of channeltrons.

In practice, filters 266 and 267 may not be individual filters, but filters on respective filter wheels, so that one particular filter can be selected simply by rotating the wheel. In this way, the machine can easily be configured to detect different wavelengths.

General-purpose computer 268 may direct the operation of the various electronics units through a multi-pin connector 260 to control the actuators, and CCD harness 262 to acquire the signal from each camera detector. The general purpose PC also controls laser pulse timing, if a pulsed laser is used. The blood is delivered to the chip and the waste and sorted cells are taken away from the chip through the set of plumbing tubes, 270, typically made of polyimide-jacketed quartz or a polymer material such as polyetheretherketone (PEEK), and glued into the MEMS chip.

Figure 5:
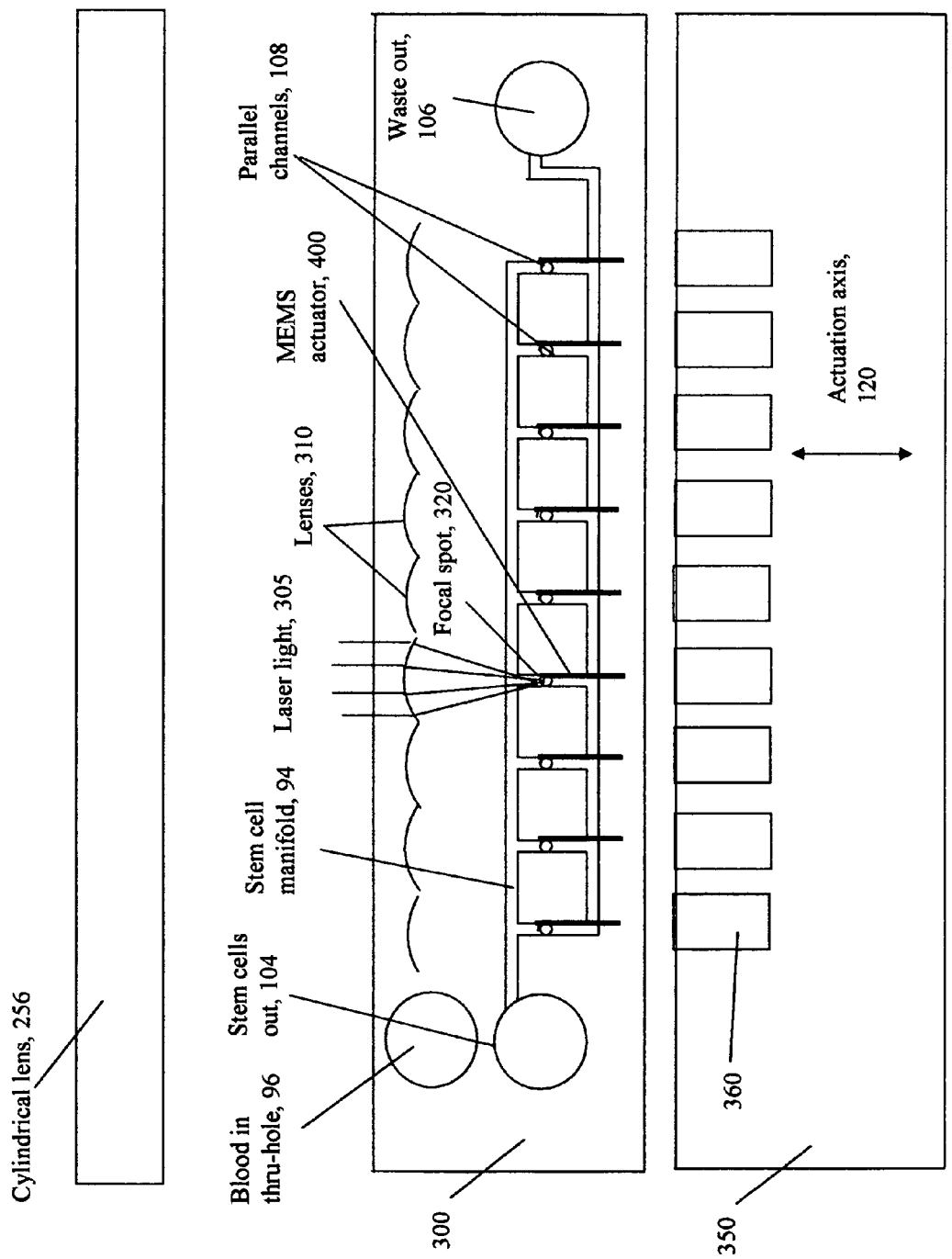
FIG. 5 is a diagrammatic view of a one-dimensional MEMS particle sorting system, showing a set of refractive lenses.

As was mentioned above, the n x m array of parallel channels and actuators may also be a one-dimensional 1×32 array, for example, of parallel channels and actuators as shown in FIG. 5. FIG. 5 shows the optical layer 80, actuator layer 100 and manifold layer 90 in plan view. The actuators 400 may be of the extensible/retractable type, rather than the pivoting type 92 as was shown in FIG. 3, and may move along the actuation axis 120 shown in FIG. 5. There may be several advantages of the arrangement shown in FIG. 5. For example, the extensible/retractable actuator may be simpler to build, and may also have the actuator formed in two pieces, an actuator portion 400 formed on MEMS chip 300 and a force-generating portion 360 formed on force-generating chip 350. Using this approach, each of the actuator portion 400 and the force-generating portion .360 may be optimized independently, as taught in co-pending U.S. application Ser. No. 11/260,367, filed on an even date herewith and incorporated by reference in its entirety. In addition, the one-dimensional MEMS particle sorting chip 300 also allows the laser light to be brought from a line focus to a focus at a plurality of single points, which may have advantages in terms of the timing of the movement of the actuator portion 400.

In particular, the laser light 305 depicted in FIG. 5 may enter the one-dimensional MEMS particle sorting chip 300 in substantially a single plane, and pass through one of a set of lenses 310. Lenses 310 may be refractive lenses, and may focus sections of the laser light 305 down to, for example, a single spot at a well-defined point 320 prior to the opening of the parallel channel 108. The detection of fluorescence by the photodetectors 264 and 265 then indicates that a target cell, for example, a human hematopoietic stem cell, is in a well-defined location relative to the actuator 400. The detection of the fluorescence event may then set the timing sequence of the subsequent actuator 400 movement with greater precision, thereby improving the accuracy of the cell sort and the purity of the sorted sample. It should be appreciated that the lenses 310 may be formed integrally with the particle sorting chip, using a transmissive material, with, for example, a higher index of refraction than air. As one exemplary embodiment, lenses 310 may be formed of a transmissive photoresist such as SU8. SU-8 is a high contrast, epoxy-based photoresist developed by IBM of Armonk, N.Y. The index of refraction of SU-8 is 1.5-1.7 from about 380 nm to about 750 nm, and SU-8 may be virtually transparent over this range. Alternatively, the optically transparent material may be any optically transparent material such as quartz, silica, alumina, indium-tin-oxide or glass, which may be formed to have at least one optically reflective and/or optically refractive surface.

Figure 6:
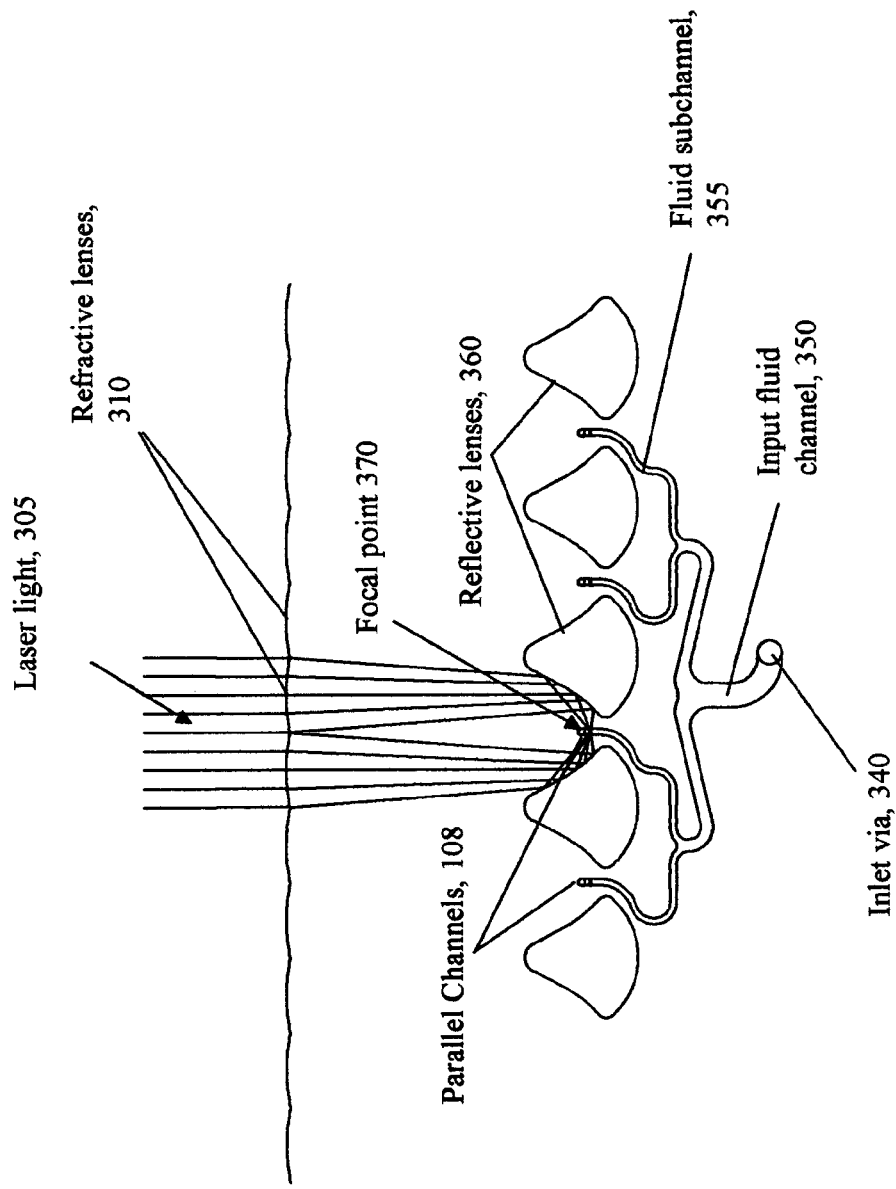
FIG. 6 is a more detailed view of the optical path of the MEMS particle sorting chip showing the input manifold.

The optical lens system may include reflective as well as refractive surfaces. FIG. 6 shows an exemplary embodiment of an optical system having both reflective and refractive optics on the particle sorting chip 300. As shown in FIG. 6, the sample fluid may enter the optical layer through an input via 340, and may traverse the optical layer to the parallel channels 108 in a confined fluid channel 350. In FIG. 6, the orientation of the axis of the parallel channels is into the paper, similar to the configuration shown in FIG. 2. Therefore, the flow of the fluid is parallel to the paper while the fluid is in the fluid channels 350 and subchannels 355, but perpendicular to the paper while the fluid is in the parallel channels 108. The propagation plane of the laser light 305 is in the plane of the paper. The four fluid subchannels 355 may be so dimensioned that the resistance to flow is the same in each of the four subchannels 355 leading from the primary fluid channel 350. Therefore, each subchannel 355 may deliver the same volume of sample fluid to each parallel channel 108.

The laser light 305 may enter the optical layer through a refractive lens 310 before impinging upon a reflective lens 360. For simplicity of manufacture, refractive lens 310 and reflective lens 360 may have the same material interface, such as air/SU-8. The structure designated as 360 may be a void etched in the SU-8, and subsequently filled with ambient air.

As the light rays 305 enter the SU-8 material, they are refracted by the refractive lens surface 310, because the index of refraction of the SU-8 is higher than the index of refraction of air. However, as the light ray travels through the SU-8 layer and impinges on structure 360, because the angle of incidence of the refracted ray may be shallower than the critical angle, and the index of refraction of the SU-8 is higher than that of air, the light ray may be reflected by total internal reflection at the SU-8/air boundary 360. Therefore, this boundary acts as a reflective surface, and may be shaped so that, in combination with refractive surface 310, the light is focused at a point 370 at or near the entrance to one of the parallel channels 108. For example, if the focal distance of the refractive lens 310 is infinity, the shape of the reflective lens 360 may be substantially parabolic. For refractive lenses 310 having finite focal lengths, the shape of the boundary of the reflective surface 360 may be adjusted to achieve focus at the point 370. For a spherical refractive surface 310, the reflective surface 360 may be a substantially straight line.

The refractive lens 310, reflective lens 360 and input channels 350 and 355 may be formed using standard lithographic patterning techniques in the SU-8 photoresist. For example, the SU-8 photoresist may be exposed with near ultra-violet radiation (350 nm to 400 nm) through a mask with features corresponding to the input channels 35 and 355, refractive lenses 310 and reflective lenses 360. The exposed and subsequently cross-linked portions of the SU-8 photoresist may be rendered insoluble to liquid developers. Accordingly, SU-8 is a negative photoresist, wherein the unexposed portions are developed and dissolved. The cross-linking occurs during exposure and subsequent baking at between about 65 degrees centigrade and about 260 degrees centigrade.

The optical layer 80 may actually consist of two parts: a glass wafer 81 patterned with chrome to make the slits and then coated with the optically transparent SU8 layer 88. The layer containing the parallel channels 108 may then be made by bonding a composite silicon-on-insulator (SOI) wafer to the SU8. A silicon-on-insulator wafer is a composite wafer which includes a thick, for example, 625 $\mu M$ silicon "handle" wafer, covered with a 1 $\mu m$ thick silicon dioxide layer and a 50 $\mu m$ thick "active" layer. The handle wafer of the SOI wafer is then etched away, followed by removal of the buried oxide, and then patterning and etching the parallel channel layer to allow fluid connections between the optical 80 and actuator 100 layers.

After processing, the optical layer 80 may be assembled with the actuator layer 100 and the manifold layer 90 to form the MEMS cell sorter chip 300, as was shown in FIG. 5. The actuator layer 100 may be made according to the systems and methods set forth in U.S. Pat. No. 6,838,056 (the '056 patent) and in co-pending U.S. application Ser. No. 11/260, 367 hereby incorporated by reference in its entirety. The manifold layer 90 may be made separately from the actuator layer 100 and optical layer 80. The manifold layer 90 may be made from another SOI wafer, in which the through wafer vias are first created in the handle wafer. The buried oxide and active layers are then removed from the SOI wafer, and the bond line is patterned on top of the wafer. The manifold structure is then patterned and etched.

The assembly of manifold, actuator and optical layers to form the MEMS cell sorter chip 300 is also described in the incorporated '056 patent. In addition to the bonding methodology described in the incorporated '056 patent, bonding may also be accomplished using a 2 $\mu m$ thick layer of a negative photoresist such as SINR, manufactured by Shi-netsu of Tokyo, Japan, and bonding the wafers at elevated temperatures as described in the incorporated '056 patent. The fluorocarbon lubricant may also be vapor-deposited rather than dip-coated, to avoid coating the bond line with lubricant which may otherwise interfere with the bonding.

Figure 7:
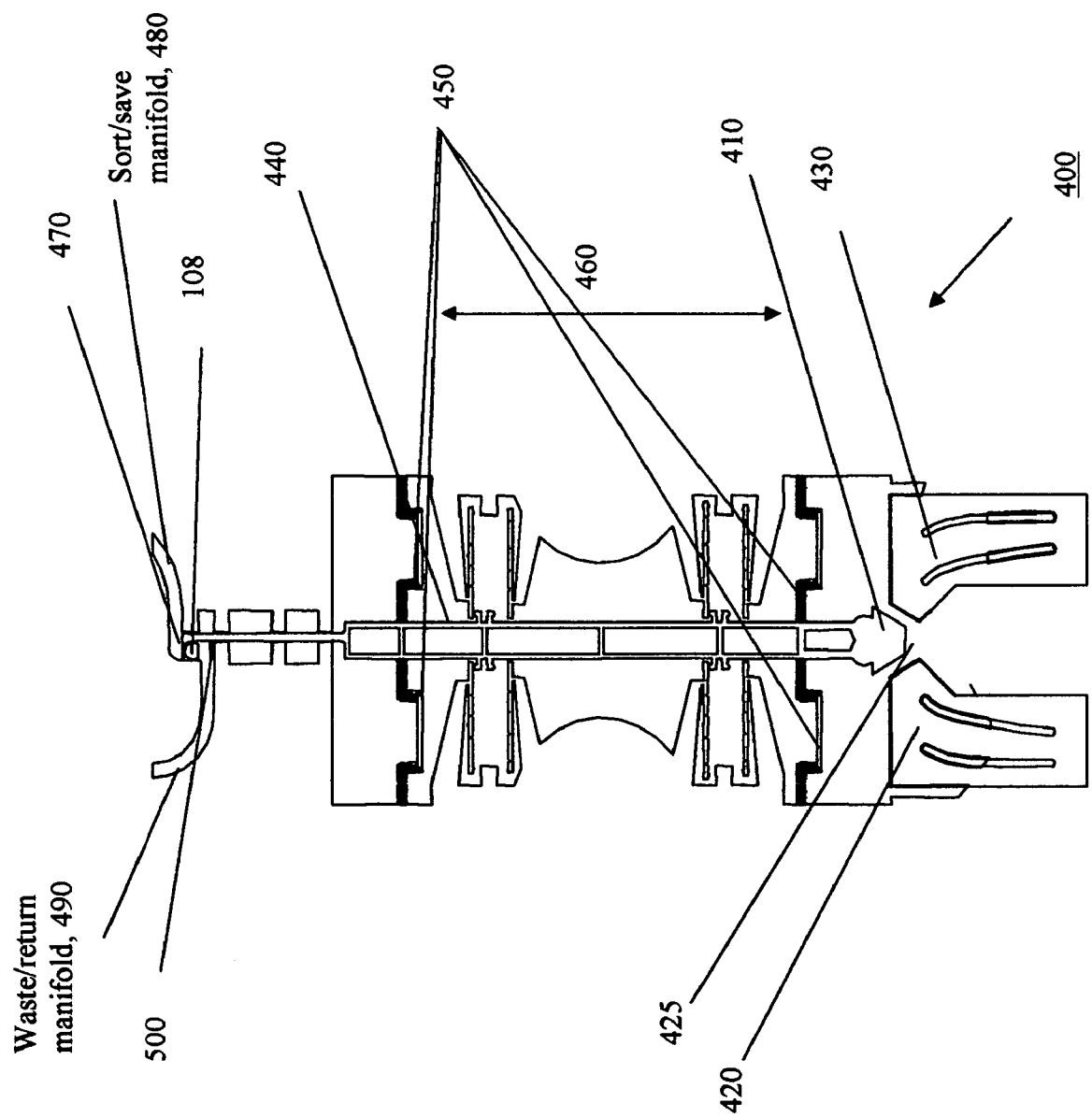
FIG. 7 is a more detailed view of the extensible/retractable actuator shown in FIG. 5.

FIG. 7 shows an exemplary embodiment of an extensible/retractable actuator 400 usable in the configuration shown in FIG. 5. The extensible/retractable actuator 400 may be an electromagnetic actuator with a magnetizable portion 410. The magnetizable portion 410 may interact with a pair of magnetizable poles, left pole 420 and right pole 430. The poles 420 and 430 and magnetizable portion 410 may be magnetized by a set of coils (not shown) would around another set of poles adjacent to and abutting poles 420 and 430. When the coils are energized, magnetic flux may arise in the poles and across a gap 425 between pole 420 and pole 430. The flux may interact with magnetizable portion 410, drawing magnetizable portion 410 into the gap between the poles 420 and 430. Therefore, the motion of the extensible/retractable actuator 400 may be along the axis 460. This action may retract the body 440 of extensible/retractable actuator 400, to which a narrow lip 470 is attached to the top of body 440. The lip 470 is then drawn to below the parallel channel 108, causing the flow of sample fluid to be directed upward into sort path 480, since lip 470 blocks the downward flow path. When the coils are not energized, the extensible/retractable actuator is released from the gap, and because of a set of hingedly mounted springs 450, the extensible/retractable actuator returns to its nominal starting position. The hingedly mounted springs 450 may be essentially identical beams, each with four 90 degree bends which allow the beam to flex in the direction 460 shown in FIG. 7.

Therefore, when the coils are not energized and the magnetizable portion 410 is withdrawn from the gap 424 by the action of the springs 450, and the lip 470 is positioned above the parallel channel 108, directing the fluid flow into the waste/return reservoir fed by waste/return manifold 490. Because the quiescent state of extensible/retractable actuator 400 is in the position shown in FIG. 7, the default situation is to not sort the cell or particle, that is, to direct the cell into the waste/return manifold. While this configuration is preferred in order to achieve a low rate of contamination of the sorted cells, it should be understood that other embodiments may be contemplated, in which the default position is the sort/save position rather than the waste/return position.

Figure 8:
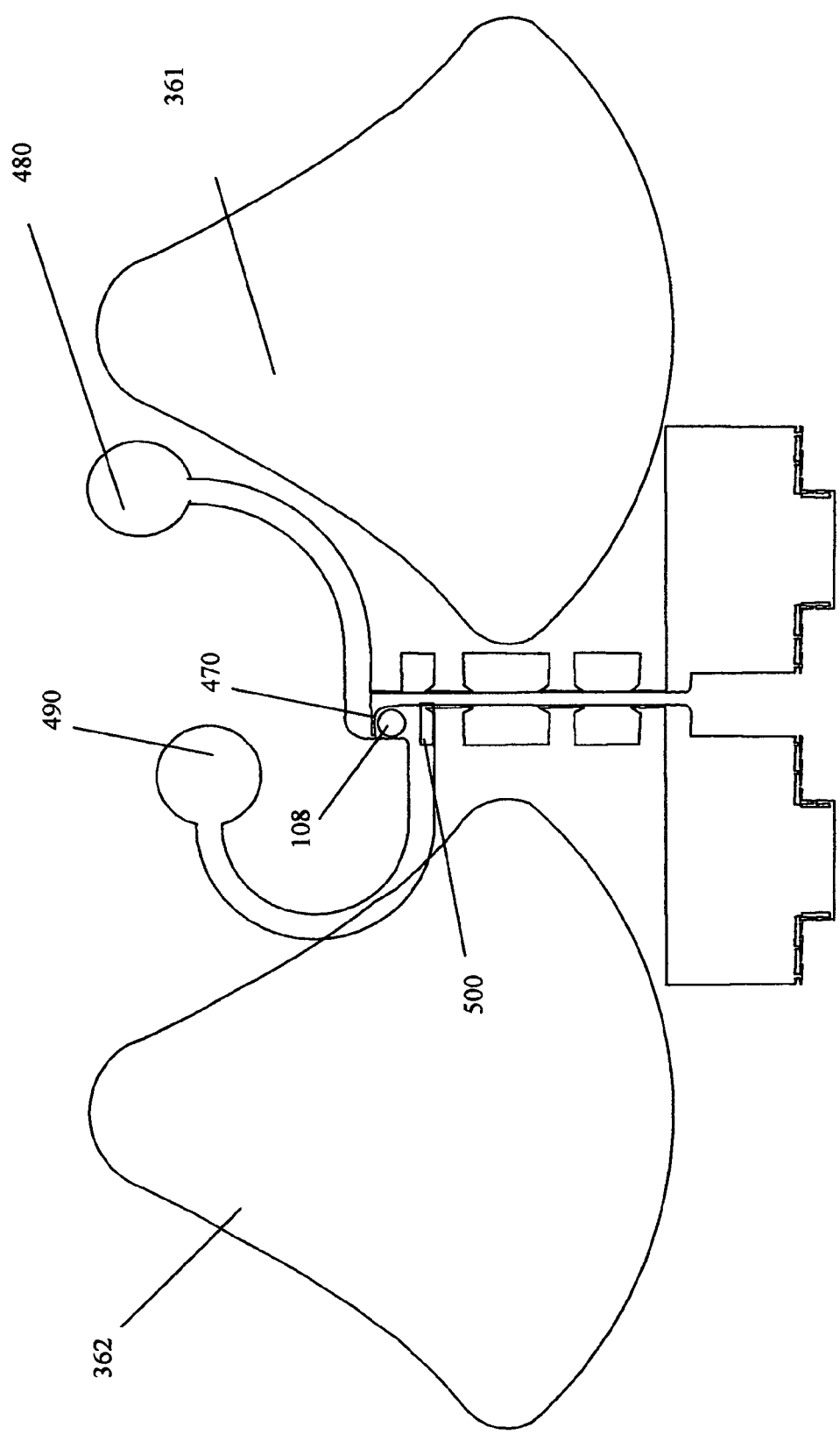
FIG. 8 is a more detailed view of the reflective surfaces in the MEMS particle sorting chip and a detection slit.

FIG. 8 shows further detail of the relative positions of the reflective lenses 360 and parallel channels 108. FIG. 8 also shows the placement of a detection slit 500 before the parallel channel 108. Detection slit 500 provides an aperture through which the fluorescent light must pass in order to reach either of detectors 264 or 265. The detection slit 500 may be formed in light reflecting layer 198. The right reflective lens 361 and left reflective lens 362 may be placed symmetrically about detection slit 500. Thus, in particular, only when an appropriately marked cell or component of interest is located within detection slit 500 and immersed in laser light 305, the cell or component of interest will fluoresce, emitting one or more photons that will be collected by collection lens 260 and directed into detectors 264 or 265. Since the arrival time of the photon is known precisely from the response of detector 264 or 265, the opening of actuator 400 may be timed precisely. The dimensions of the detection slit may be, for example, about 4 μm long and about 25 μm wide.

Figure 9:
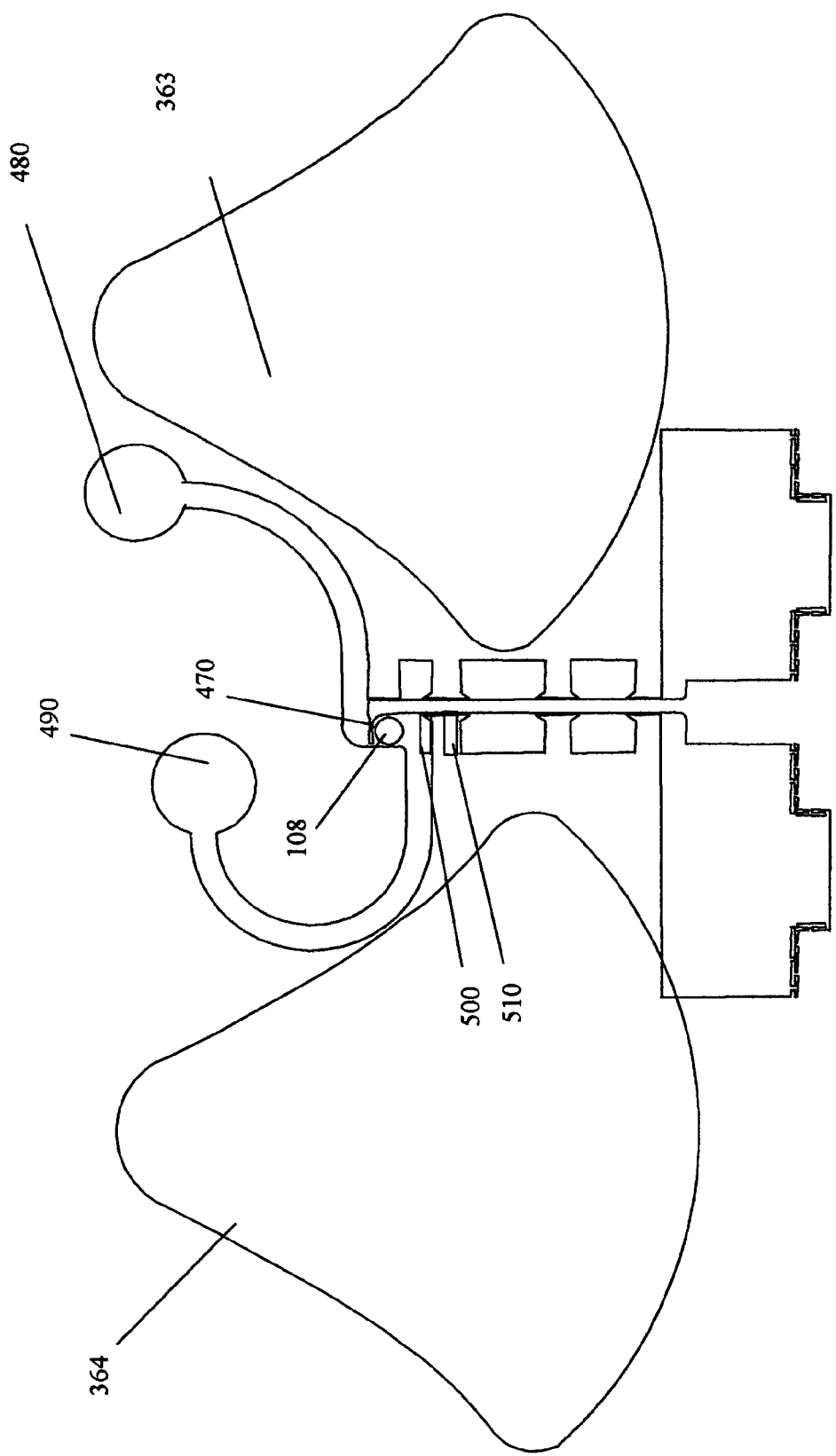
FIG. 9 is a more detailed view of the reflective surfaces of the MEMS particle sorting chip showing two detection slits.

FIG. 9 illustrates another exemplary embodiment of the reflective lenses 360 and detection slit 500. In FIG. 9, detection slit 500 is accompanied by a second detection slit 510. Right-side reflective optical element 363 may be disposed and shaped to focus laser light 305 onto detection slit 500, whereas left-side reflective optical element 364 may be disposed and shaped to focus laser light 305 onto detection slit 510. Since the right-side 363 and left-side 354 optical elements are now displaced relative to the detection slits, another reflective surface may also be placed at the far side of each respective detection slit, to intercept and reflect laser light that passes under each detection slit. These reflective surfaces will reflect the laser light back toward the laser source. This may reduce the amount of scattered laser light within the chip, and reduce the chances of photobleaching the fluorophores on the cells. Left-side refractive lenses (not shown in FIG. 9) may also have their contours adjusted to accommodate the longer focal length of the left-side detection slit 510 relative to right-side detection slit 500. By having two separate detection slits 500 and 510, the velocity of the cell or particle of interest in the fluid flow may be measured, allowing once again, more accurate timing of the opening of extensible/retractable actuator 400. For example, knowing the distance between detection slit 510 and detection slit 500 and the timing of the fluorescence signal emanating from each of detector slits 500 and 510, the velocity of the particle may be ascertained. Given that velocity, and the distance in the flow path between detection slit 500 or detection slit 510 and extensible/retractable actuator lip 470, the exact timing of the retraction of extensible/retractable actuator 400 can be known. Therefore, extensible/retractable actuator 400 may only be activated when a human hematopoietic stem cell or component of interest requires sorting from the fluid stream. Also, given the velocity of the particle, an estimate of the particle size may be ascertained by deconvolving the effects of particle velocity from the time-dependent fluorescent signal from either of detectors 264 or 265.

Figure 10:
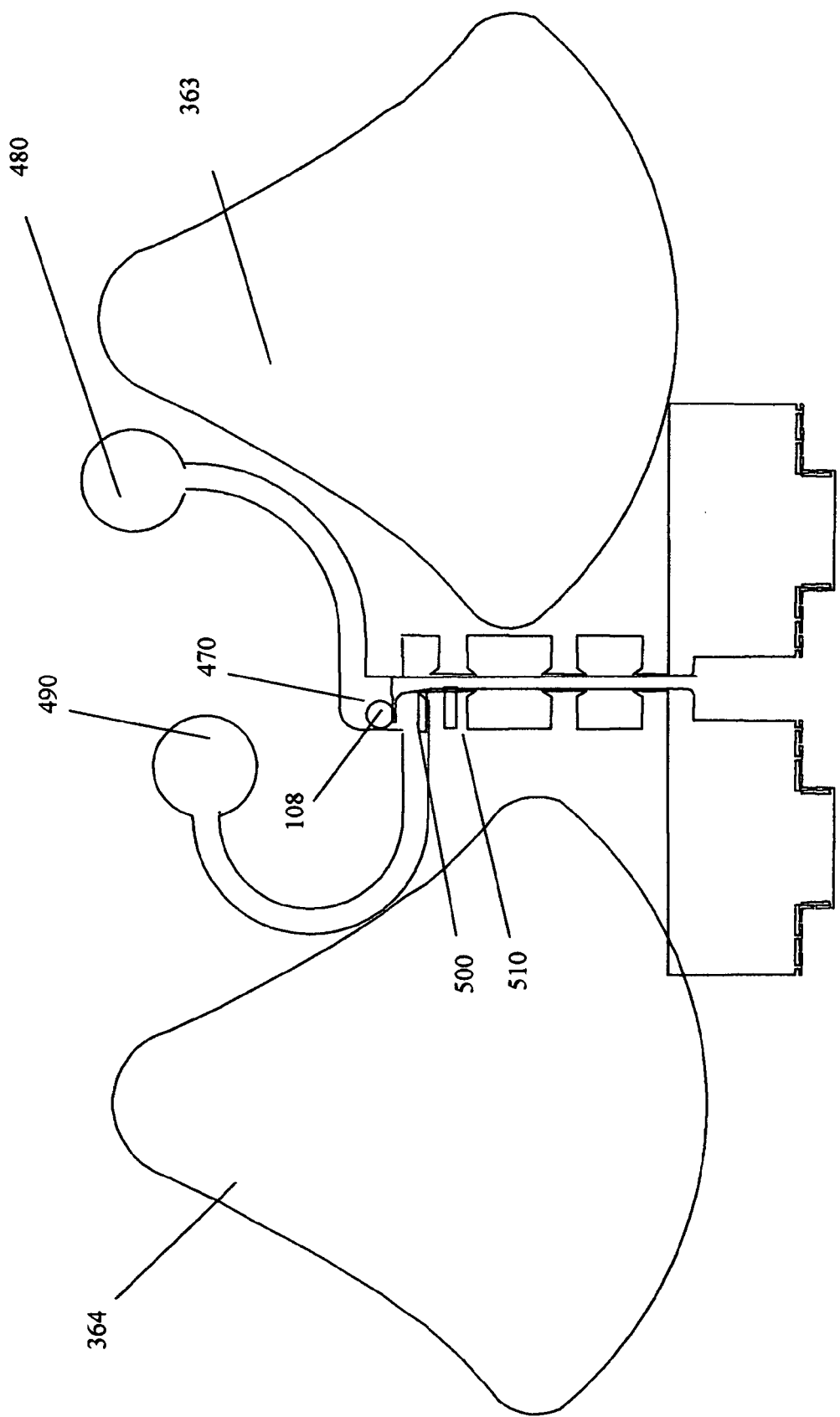
FIG. 10 is a more detailed view of the reflective surface of the MEMS particle sorting chip with the MEMS actuator in the sort position.

FIG. 10 shows the activation of extensible/retractable actuator 400, in response to the detection of a cell or component of interest within a detection slit 500 or 510. When a cell or component is detected, its velocity if calculated, and the amount of time required for the cell or particle of interest to reach the parallel channel 108 is ascertained. The coils of the extensible/retractable actuator may then be activated at or slightly before that time. The energizing of the coils may cause magnetic flux to be generated in the magnetizable poles, 420 and 430, drawing the magnetizable portion 410 into the gap 425 between the poles. The magnetizable portion 410 is coupled to the body 440 and lip 470, which causes the lip 470 to be drawn down as shown in FIG. 10. The lip 470 then blocks the downward flowing path into the waste/return manifold 490, and directs the cell or particle instead into the sort/save manifold 480.

Figure 11:
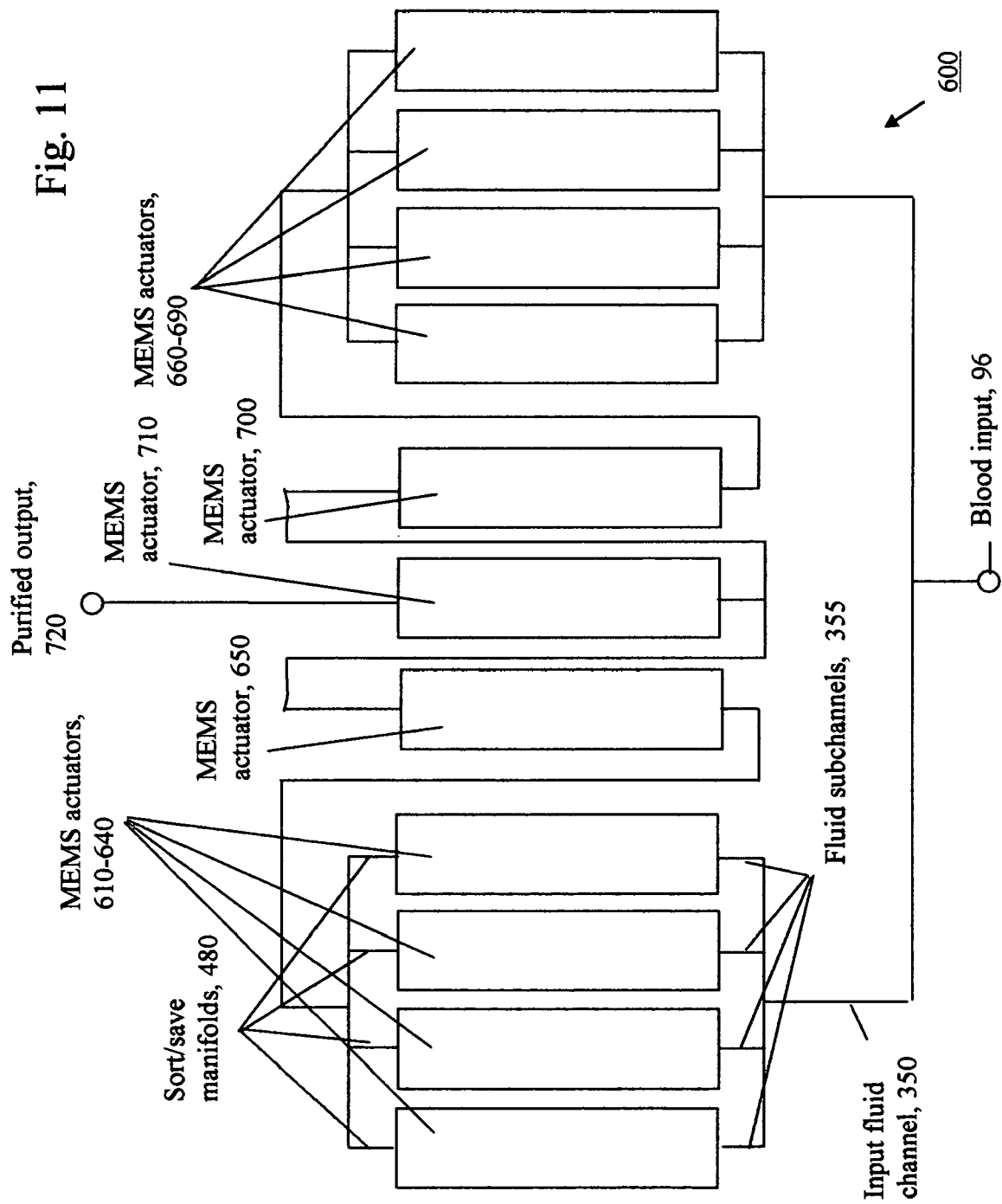
FIG. 11 is a schematic diagram of a plurality of MEMS actuators coupled to a single input stream in parallel, with the output of at least one MEMS actuator serving as the input to at least one other MEMS actuator.

While FIGS. 1 and 3 show each MEMS actuator being connected in parallel to the blood input 96 to maximize sorting speed, it should be understood that the MEMS actuators 92 may also be ganged or arranged partly in parallel, and partly serially, to accomplish other objectives. For example, FIG. 11 shows a 1×11 array of MEMS actuators, wherein two sets of four actuators each are coupled to a single input, such as blood input 96. The MEMS actuators 610-640 may be of the extensible/retractable type 400 shown in FIG. 7, or the pivoting type 92 shown schematically in FIGS. 1 and 3, for example. The four fluid subchannels 355 couple the fluid from the input fluid channel 350 to each of the four MEMS actuators 610-640 in parallel. The output of each of MEMS actuators 610-650 is then combined in sort/save manifolds 480, and together are routed to the input of a fifth MEMS actuator 650. In this manner, MEMS actuator 650 sorts a fluid sample which has already been sorted by MEMS actuators 610-640. The output of MEMS actuator 650 may therefore be expected to be of higher purity than the output of any of MEMS actuators 610-640.

In a similar manner, the blood input 96 is coupled in parallel to the input manifolds of MEMS actuators 660-690. The sort/save output of MEMS actuators 660-690 is then combined as input to MEMS actuator 700. In this manner, MEMS actuator 700 sorts a fluid sample which has already been sorted by MEMS actuators 660-690. Therefore, the output of MEMS actuator 700 may be expected to be of higher purity than the output of any of MEMS actuators 660-690.

In a similar manner, the output of MEMS actuators 650 and 700 may be combined as input to a final MEMS actuator 710. This MEMS actuator 710 may produce the final, purified output 720.

Any number of variations of the configuration shown in FIG. 11 may be envisioned. For example, fewer or more MEMS actuators may be connected in parallel to determine the overall throughput of the device. Fewer or more MEMS actuators may then be connected in series to increase the sort purity of the output. Therefore, the arrangement of MEMS devices in series or in parallel will depend on the desired performance characteristics of the device, in terms of, for example, sort purity and throughput.

While various details have been described in conjunction with the exemplary implementations outlined above, various alternatives, modifications, variations, improvements, and/or substantial equivalents, whether known or that are or may be presently unforeseen, may become apparent upon reviewing the foregoing disclosure. While the embodiment described above relates to a microelectromechanical human hematopoietic stem cell sorter, it should be understood that the techniques and designs described above may be applied to any of a number of particle sorting applications. Other actuation means may be envisioned in addition to electromagnetic, including electrostatic, and fluidic. Particle sorting chips including n×m arrays of microelectromechanical actuators and parallel channels, as well as one-dimensional 1×m arrays of such microelectromechanical actuators and parallel channel are contemplated according to the systems and methods described here. Furthermore, details related to the specific design features of the microelectromechanical actuator and particle sorting chip are intended to be illustrative only, and the invention is not limited to such embodiments. Accordingly, the exemplary implementations set forth above, are intended to be illustrative, not limiting.

What is claimed is:

1. A micromechanical particle sorting chip, comprising:
   at least one fluid channel defined in an optically transparent layer formed over a substrate;
   at least one of a reflective surface and a refractive surface formed in the optically transparent layer, which focuses light to a focal point within the fluid channel; and
   at least one micromechanical actuator defined on the substrate, disposed to direct a particle of interest from a fluid stream at a point downstream of the focal point within the fluid channel, into one of a plurality of possible exit paths located in the substrate.

2. The micromechanical particle sorting chip of claim 1, wherein both a reflective and a refractive surface are formed in the optically transparent layer.

3. The micromechanical .particle sorting chip of claim 1, further comprising:
   a first detection slit disposed along the fluid channel which limits an aperture from which light from the fluid channel may be collected.

4. The micromechanical particle sorting chip of claim 3, further comprising at least one additional detection slit located adjacent the first detection slit along the fluid channel.

5. The micromechanical particle sorting chip of claim 1, further comprising a plurality of substantially parallel channels which direct a fluid stream from the at least one fluid channel to the point at which the at least one micromechanical actuator directs.

6. The micromechanical particle sorting chip of claim 1, wherein the refractive surface is substantially spherical, and the reflective surface is substantially parabolic.

7. The micromechanical particle sorting chip of claim 1, wherein the optically transparent layer comprises an epoxy-based photoresist.

8. The micromechanical particle sorting chip of claim 1, wherein each actuator has an input manifold and an output manifold, and the input manifolds of two or more actuators are coupled together in a parallel arrangement.

9. The micromechanical particle sorting chip of claim 8, wherein the output of at least one micromechanical actuator provides an input fluid stream to at least one other micromechanical actuator.

10. The micromechanical particle sorting chip of claim 1, wherein the actuator is an electromagnetic actuator.

11. A method of manufacturing a micromechanical particle sorting chip, comprising:
    forming at least one fluid channel in an optically transparent layer formed over a substrate;
    forming at least one of a reflective surface and a refractive surface in the optically transparent layer, which focuses light to a focal point within the fluid channel; and
    forming at least one micromechanical actuator defined on the substrate, disposed to direct a particle of interest from a fluid stream at a point downstream of the focal point within the fluid channel, into one of a plurality of possible exit paths located in the substrate.

12. The method of claim 11, wherein forming the at least one of a reflective surface and a refractive surface in an optically transparent layer comprises forming at least one of a reflective surface and a refractive surface in an optically transparent photoresist using photolithographic techniques.

13. The method of claim 11, further comprising forming at least one detection slit along the fluid channel upstream of the micromechanical actuator.

14. The method of claim 11, further comprising:
    forming a plurality of parallel channels which direct a fluid stream from the at least one fluid channel to the micromechanical actuators.

15. The method of claim 11, further comprising coupling an input manifold of a plurality of actuators to a source of a fluid sample in parallel.

16. The method of claim 11, further comprising coupling an output of at least one actuator to an input of at least one other actuator.

17. A method for sorting a particle of interest from a fluid sample, comprising:
    applying a fluid sample to a fluid channel defined in an optically transparent layer formed over a micromechanical particle sorting chip;
    applying laser light through at least one of a reflective and a refractive surface formed in the optically transparent layer, and directing the laser light to a focus at a detection slit in the fluid channel;
    detecting a fluorescence signal generated by the particle of interest emitted through the detection slit;
    actuating a micromechanical actuator located on the micromechanical particle sorting chip and disposed adjacent to the optically transparent layer to direct the particle of interest into one of a plurality of possible exit paths located in the sorting chip.

18. The method of claim 17, further comprising:
    measuring a first time-dependent fluorescence signal arriving at a detector from a first detection slit;
    measuring a second time-dependent fluorescence signal arriving at the detector from a second detection slit; and
    calculating the velocity of the particle of interest in the fluid sample based on the first time-dependent and second time-dependent fluorescence signals.

19. The method of claim 18, further comprising:
estimating the size of the particle of interest based on the calculated velocity and a shape of at least one of the first and the second time-dependent fluorescent signals.

20. The method of claim 17, further comprising:
forming a presorted fluid stream by coupling the one of the plurality of possible exit paths of a first micromechanical actuator to one of a plurality of possible exit paths from a second micromechanical actuator; and
coupling the presorted fluid stream to an input channel of a third micromechanical actuator.

* * * * *